United States Patent [19]

Sommercorn et al.

[11] Patent Number: 4,543,087
[45] Date of Patent: Sep. 24, 1985

[54] DOUBLE LUMEN CATHETER TIP

[75] Inventors: Richard K. Sommercorn; Wayne E. Quinton, both of King County, Wash.

[73] Assignee: Quinton Instrument Company, Seattle, Wash.

[21] Appl. No.: 551,102

[22] Filed: Nov. 14, 1983

[51] Int. Cl.$^4$ .................................................. A61M 5/00
[52] U.S. Cl. ........................................ 604/43; 604/264
[58] Field of Search ................................ 604/43–45, 604/53, 93, 173, 264, 280–284

[56] References Cited

U.S. PATENT DOCUMENTS

| D. 272,651 | 2/1984 | Mahurkar | 604/44 X |
| 998,339 | 7/1911 | Hollins | |
| 1,045,326 | 11/1912 | Ruflin | 604/43 |
| 2,230,218 | 2/1941 | Asche | 604/43 |
| 2,564,977 | 8/1951 | Quang Hsi Hu | 128/218 |
| 2,590,895 | 4/1952 | Scarpellino | 128/221 |
| 2,625,932 | 1/1953 | Salisbury | 128/214 |
| 3,324,853 | 6/1967 | Czorny | 128/214.4 |
| 3,463,152 | 8/1969 | Sorenson | 128/214.4 |
| 3,756,234 | 9/1973 | Kopp | 128/214 R |
| 3,804,097 | 4/1974 | Rudie | 128/350 R |
| 3,830,234 | 8/1974 | Kopp | 128/214 R |
| 4,027,668 | 6/1977 | Dunn | 128/214 R |
| 4,098,275 | 7/1978 | Consalvo | 128/214 R |
| 4,134,402 | 1/1979 | Mahurkar | 128/214 R |

FOREIGN PATENT DOCUMENTS

| 2259865 | 6/1974 | Fed. Rep. of Germany . | |
| 592193 | 4/1925 | France . | |
| 2285148 | 4/1976 | France | 604/43 |

Primary Examiner—Stephen C. Pellegrino
Attorney, Agent, or Firm—Seed and Berry

[57] ABSTRACT

A double lumen catheter having a fluid intake lumen and fluid return lumen of equal cross-sectional area, separated by an internal divide wherein blood flow characteristics are increased and maintained in a continuous fashion by a series of apertures positioned on both the intake side and return side of the catheter is disclosed. The apertures are in such position and configuration that they communicate with one another to prevent the accumulation of fibrin or other matter within the lumens as fluid enters into or exits from those lumens.

4 Claims, 5 Drawing Figures

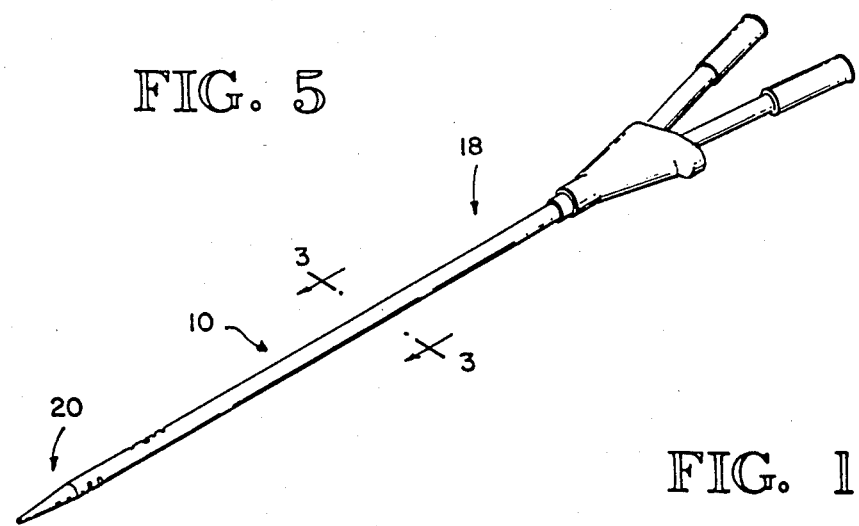
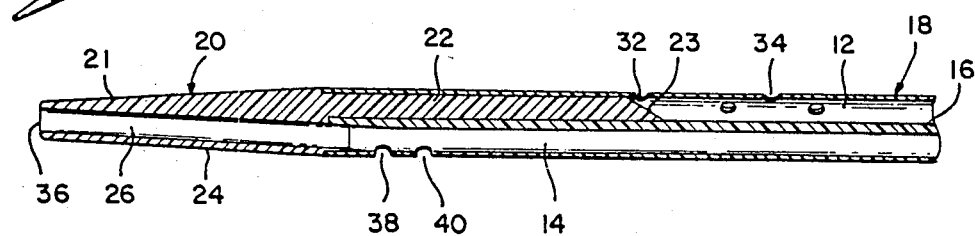
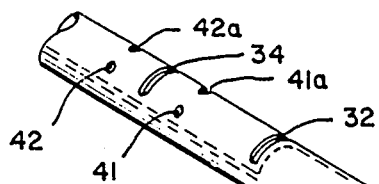
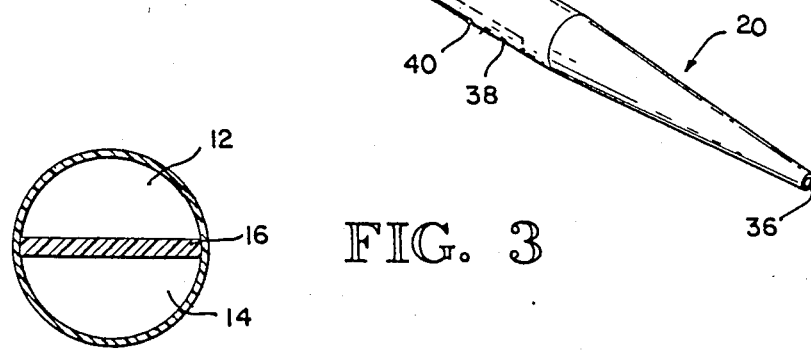

DOUBLE LUMEN CATHETER TIP

TECHNICAL FIELD

The present invention relates to an improved double lumen catheter for use in hemodialysis, and, in particular, to a double lumen catheter having a plurality of apertures communicating with or among one another to prevent the accumulation of fibrin or other matter as well as reducing the potential for aeration.

BACKGROUND ART

The prior art reveals several methods by which blood or other fluids can be withdrawn and returned to the body. First, the conventional way employs two separate needles, as in U.S. Pat. No. 2,625,932 or two adjoining tubes, as in U.S. Pat. No. 4,098,275. When employing this technique, the two needles must be spaced apart a sufficient distance so as to prevent the cleansed blood from reentering the blood outlet needle and returning to the dialysis machine, but must be sufficiently close to each other to prevent the vein or fistula from collapsing. The prior art also discloses various methods for single-needle dialysis. Examples of this method may be found in U.S. Pat. Nos. 3,756,234 and 3,830,234. However, single-needle dialysis requires operation within only limited flow rates, and further requires that blood be both extracted and returned through the same needle, leaving this procedure not suitable for all patients. A third known manner employs a double lumen catheter to gain the advantage of a conventional two-needle system while requiring only one puncture.

While the use of a double lumen catheter as exhibited by U.S. Pat. No. 4,134,402, has been an advance over the conventional manner of performing dialysis, the problems of recycling, clotting, special equipment requirements, and inadequate flow rates remain. Accordingly, it is the primary object of the present invention to provide an improved catheter capable of eliminating the potential for aeration or clotting of blood as well as increasing the blood flow potential over other double lumen designs.

Other objects and advantages of the invention will become apparent on reading the following detailed description and upon reference to the attached drawings.

DISCLOSURE OF INVENTION

The present invention comprehends a flexible double lumen catheter comprised of a fluid intake lumen and fluid return lumen of equal size separated by means of an internal divider, the fluid intake lumen having a plurality of apertures positioned in such a manner to prevent the accumulation of fibrin or other matter within the intake lumen, and the fluid return lumen having a pair of spaced apertures positioned in such a manner to prevent the accumulation of fibrin or other matter within the lumen as fluid exits from the lumen through those apertures.

The invention also comprehends a preformed tip having a beveled end to ease the insertion into the vein as well as a stepped proximal end adaptable for insertion into the opened blunt end of the catheter. This tip is provided with a beveled edge on a first portion at its proximal end to prevent the occlusion of fluid entering the fluid intake lumen, as well as a second portion having an open ended channel which communicates with the fluid return lumen to allow for the flow of fluid outwardly from the fluid return lumen.

The present invention provides more favorable flow pressure characteristics while, at the same time, maintaining the advantages of a double lumen catheter.

BRIEF DESCRIPTION OF THE DRAWINGS

FIG. 1 is a vertical cross-section of a catheter.

FIG. 2 is an isometric illustration of the fluid intake side of the catheter shown in FIG. 1.

FIG. 3 is an enlarged horizontal cross-sectional view taken substantially along the line 3—3 of FIG. 5.

FIG. 5 is an isometric view of the catheter of FIG. 1.

BEST MODE FOR CARRYING OUT THE INVENTION

Figure 4:
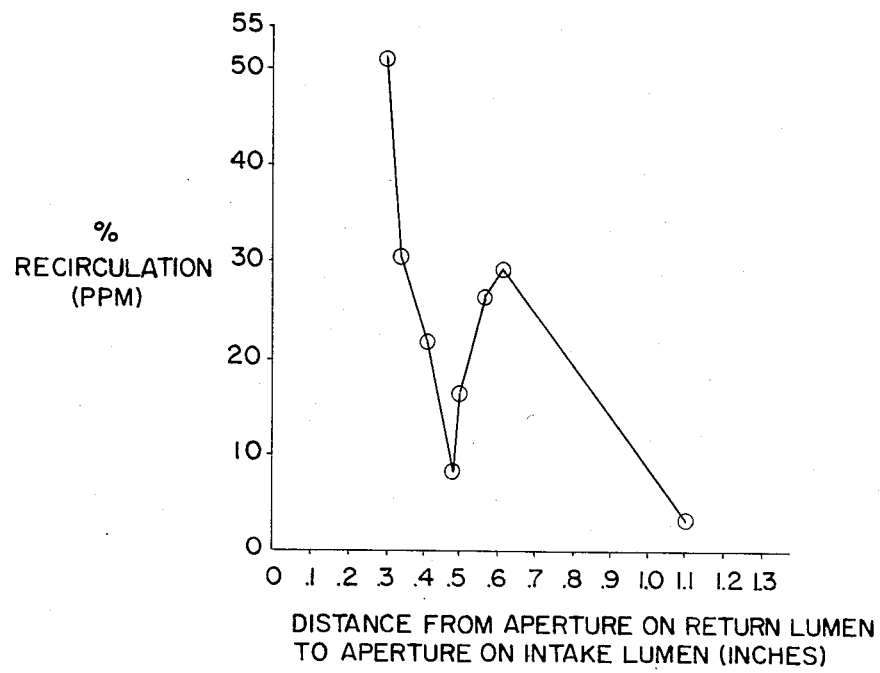
FIG. 4 is a graph illustrating the most advantageous fluid flow characteristics of catheters of this invention.

In reference to FIG. 1, catheter 10 therein shown comprises a fluid intake lumen 12 and fluid return lumen 14 of equal cross-sectional area separated by internal divider 16 which extends the entire length of tube 18. Tube 18 is preferably flexible, nontoxic, biologically neutral, and essentially insensitive to medications (essentially nonabsorbent and nonadsorbent). In the region where they are contiguous, fluid intake lumen 12 and fluid return lumen 14 define a compact cross-section typically as shown in FIG. 3. Catheter 10 is also provided with pre-formed tip 20, which can be made out of a variety of materials, for instance polyvinyl chloride or polyurethane. As illustrated in FIG. 1, pre-formed tip 20 is shown in its operative position inserted into the distal end of tube 18. Pre-formed tip 20 has at its proximal end a first portion 22 which is inserted in the fluid intake lumen 12 and carries a beveled end 23 to aid in the continuous and uninterrupted flow of fluid through aperture 32 into fluid intake lumen 12. Pre-formed tip 20 also carries at its proximal end a second portion 24, which, like first portion 22, is adaptable for insertion into the distal end of fluid return lumen 14 of catheter 10. When first portion 22 is inserted into fluid intake lumen 12 and second portion 24 is inserted into fluid return lumen 14, a seal is formed which acts to insure that no aeration or recycling of the fluid which is being treated occurs through the interface between pre-formed tip 20 and tube 18. Second portion 24 is also provided with channel 26 to allow for the flow of fluid outwardly from fluid return lumen 14 through aperture 36 provided at the distal end of pre-formed tip 20. Pre-formed tip 20 is formed with a beveled distal end 21 to ease the trauma of insertion into a vein or fistula.

As further illustrated in FIG. 1, catheter 10 contains apertures 32 and 34 located at the highest arcuate point of fluid intake lumen 12, aperture 32 being positioned just rearward of beveled end 23 of first portion 22, and aperture 34 being spaced just rearward of aperture 32, but not so far as to create any areas of reduced flow between apertures 32 and 34 within fluid intake lumen 12. Catheter 10 is also provided with spaced apertures 38 and 40 located at the highest arcuate point of fluid return lumen 14, aperture 38 being positioned just rearward of second portion 24, and aperture 40 spaced just rearward of aperture 38, but not so far as to create any areas of reduced flow between apertures 38 and 40 within fluid return lumen 14. Apertures 38 and 40 communicate with fluid return lumen 14 to aid in the continuous and uninterrupted flow of fluid exiting from fluid return lumen 14.

As shown in FIG. 2, which is an isometric view of the intake side of catheter 10, aperture 12 is positioned just rearward of beveled end 23 of first portion 22 of the proximal end of pre-formed tip 20. As previously mentioned, aperture 34 is positioned just rearward of aperture 32. Located laterally and in circumferential relationship to aperture 34 are a series of apertures 41, 41a, 42, and 42a. When catheter 10 is in use, this series of apertures aids in insuring both that the patient's vessel wall cannot obstruct the entire intake system at any one point in time and that fibrin is not deposited at the apertures opening into fluid intake lumen 12, causing partial or total blockage.

In operation, it should be noted that the cross-sectional area of any two apertures 32, 34, 38, 40, or 41, 41a, 42, and 42a is equal to or greater than the cross-sectional area of either the fluid intake lumen 12 or fluid return lumen 14. This relationship further insures that identical flow rates into and out of catheter 10 will be maintained during the entire dialysis procedure, as well as eliminating the previously required task of having the technician or physician manually rotate the catheter 10 to insure an adequate flow into and out of the respective lumens 12 and 14.

Unless the context necessarily restricts the meaning of "vessel," "vessel" should be read to mean any body cavity or passage and should not be limited to arterial, venal, lymphatic, renal, or other circulatory vessels.

The following example is intended to illustrate the most advantageous relationship between the aperture 40 on return lumen 14 and the aperture 32 on intake lumen 12. In general, the following example would be applicable to determining the relationship between the aperture positioned most rearward of the distal end on the return side of the catheter and the aperture positioned most forward to the distal end on the intake side of the catheter.

EXAMPLE 1

Flow test procedure: A small roller pump was used to pump glycerated water (to simulate viscosity of blood) at 200 Ml/min through rubber tubing with 0.25" I.D. which simulated a vein. The catheters listed in table I were inserted one at a time into a slit in the simulated vein. The roller pump of a Drake-Willock dialysis machine was utilized to simulate dialysis flow.

Glycerated water in proportion to 810 ml glycerine to 3.3 liter of de-ionized water was seeded with 2.88 gm lithium chloride (LiCl) as a tracer.

The amount of LiCl was then measured in the fluid returning through the arterial port on each catheter. The percent recirculation was then determined by dividing measured LiCl (ppm) in the arterial port by LiCl (ppm) in the venous line (baseline fluid). Table II and FIG. 4 give the computed recirculation values.

TABLE I

| CATHETER CONFIGURATION | |
| --- | --- |
| CATHETER | DISTANCE FROM RETURN APERTURE TO INTAKE APERTURE |
| 1 | .300 inch |
| 2 | .339 |
| 3 | .416 |
| 4 | .485 |
| 5 | .500 |
| 6 | .556 |
| 7 | .616 |
| 8 | 1.100 |
| BASELINE FLUID | |

TABLE II

| COMPUTED RECIRCULATION | | |
| --- | --- | --- |
| CATHETER | LiCl (ppm) | PERCENT RECIRCULATION |
| 1 | 62 | 51.60 |
| 2 | 37 | 30.80 |
| 3 | 26 | 21.60 |
| 4 | 10 | 8.30 |
| 5 | 20 | 16.60 |
| 6 | 32 | 26.60 |
| 7 | 35 | 29.17 |
| 8 | 3.8 | 3.10 |
| BASELINE FLUID | 120 | — |

As the tables within example I and the graph of FIG. 4 show, the most advantageous range in which to position the apertures on the return lumen with respect to the apertures opening into the intake lumen is at a distance of approximately 0.3–0.6 inches, but preferably 0.4–0.5 inches. Operating within this range will provide for the minimum amount of recirculation while the catheter is in operation.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A double lumen catheter comprising:

a flexible, open-ended, multichannel tube having a fluid intake lumen and fluid return lumen of equal cross-sectional area separated by means of an internal divider, said tube having a plurality of apertures positioned rearward of the distal end and opening into said intake lumen, said apertures communicating with or among one another to prevent the accumulation of fibrin or other matter within the channel, and a pair of spaced apertures opening into said fluid return lumen positioned rearward of the distal end and communicating with the fluid return lumen, said apertures communicating with or among one another to prevent the accumulation of fibrin or other matter within the channel as fluid exits from the channel through said apertures; and a preformed tip having a beveled distal end and stepped proximal end, said proximal end having a first portion adaptable for insertion into and in sealing relationship with the fluid intake lumen and terminating just forward of the apertures opening into the fluid intake lumen, said first portion having a beveled end to prevent the occlusion of fluid entering the fluid intake lumen, and a second portion adaptable for insertion into and in sealing relationship with the fluid return lumen and terminating just forward of the apertures opening into the fluid return lumen, said second portion having an open-ended channel communicating with the fluid return lumen to allow for the flow of fluid outwardly from said fluid return lumen.

2. The invention as defined in claim 1 wherein the apertures opening into said intake lumen are arranged in a configuration providing a first aperture located just rearward of the beveled end of said first portion, a second aperture spaced rearward of said first aperture and on the same plane as said first aperture, and a series of apertures located laterally and circumferentially from said second aperture.

3. The invention as defined in claim 1 wherein said channels have a selected cross-sectional area, and any two of said apertures have a cross-sectional area equivalent to or greater than the cross-sectional area of said channel.

4. The invention as defined in claim 1 wherein said plurality of apertures are positioned at the highest arcuate point of the fluid intake lumen, and said pair of spaced apertures are located directly opposite said plurality of apertures and in communication with said return lumen.

* * * * *